(12) United States Patent
Konno

(10) Patent No.: US 7,319,896 B2
(45) Date of Patent: Jan. 15, 2008

(54) CAPSULE ENDOSCOPE

(75) Inventor: Mitsujiro Konno, Hino (JP)

(73) Assignee: Olympus Corporation, Tokyo (JP)

( * ) Notice: Subject to any disclaimer, the term of this patent is extended or adjusted under 35 U.S.C. 154(b) by 389 days.

(21) Appl. No.: 10/933,315

(22) Filed: Sep. 3, 2004

(65) Prior Publication Data

US 2005/0054902 A1 Mar. 10, 2005

(30) Foreign Application Priority Data

Sep. 5, 2003 (JP) ............................. 2003-314707

(51) Int. Cl.
*A61B 5/05* (2006.01)
(52) U.S. Cl. .................. 600/407; 600/160; 348/48
(58) Field of Classification Search ................ 600/109, 600/160, 176–179, 101

See application file for complete search history.

(56) References Cited

U.S. PATENT DOCUMENTS

| | | | | |
|---|---|---|---|---|
| 3,961,844 A | * | 6/1976 | Betensky | 359/648 |
| 4,803,992 A | * | 2/1989 | Lemelson | 600/342 |
| 5,404,246 A | * | 4/1995 | Kaneko et al. | 359/649 |
| 5,428,480 A | * | 6/1995 | Betensky | 359/692 |
| 5,907,386 A | * | 5/1999 | Gupta et al. | 351/177 |
| 6,038,079 A | * | 3/2000 | Michaels | 359/661 |
| 6,134,056 A | * | 10/2000 | Nakamuka | 359/784 |
| 6,306,082 B1 | * | 10/2001 | Takahashi et al. | 600/173 |
| 6,908,427 B2 | * | 6/2005 | Fleener et al. | 600/104 |
| 6,980,427 B2 | * | 12/2005 | Garnett et al. | 361/685 |
| 2001/0051766 A1 | * | 12/2001 | Gazdzinski | 600/309 |
| 2002/0055669 A1 | * | 5/2002 | Konno | 600/167 |
| 2003/0076591 A1 | * | 4/2003 | Ohmori et al. | 359/566 |
| 2003/0158503 A1 | * | 8/2003 | Matsumoto | 600/593 |
| 2003/0171648 A1 | | 9/2003 | Yokoi et al. | |
| 2005/0043583 A1 | * | 2/2005 | Killmann et al. | 600/109 |

FOREIGN PATENT DOCUMENTS

| | | |
|---|---|---|
| JP | 2001-91860 | 4/2001 |
| WO | WO 01/65995 A2 | 9/2001 |

* cited by examiner

*Primary Examiner*—Brian L. Casler
*Assistant Examiner*—Nasir Shahrestani
(74) *Attorney, Agent, or Firm*—Arnold International; Bruce Y. Arnold

(57) ABSTRACT

A capsule endoscope is disclosed that includes a light source, an objective optical system that forms an image of an object that is illuminated by the light source, an image pickup device that receives the image formed by the objective optical system; and a transparent cover that is positioned in front of the objective optical system. Specified conditions are satisfied by the objective optical system so that objects having a shape that conforms with the shape of the transparent cover at the periphery of the field of view, as well as more distant objects on-axis, are within the depth of field of the objective optical system's field of view. The transparent cover itself is purposely kept from being within the depth of field of the objective optical system's field of view.

20 Claims, 13 Drawing Sheets

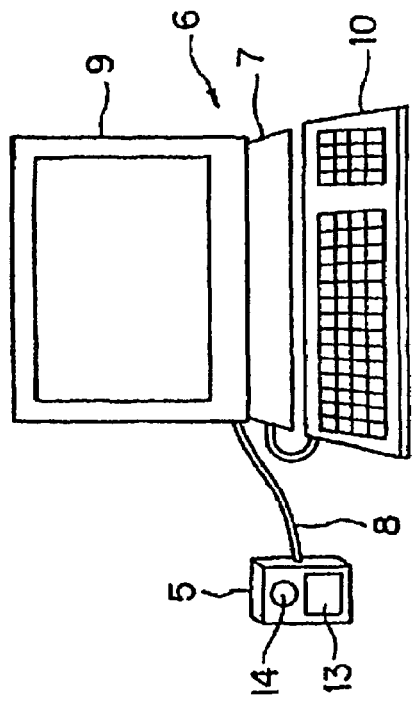
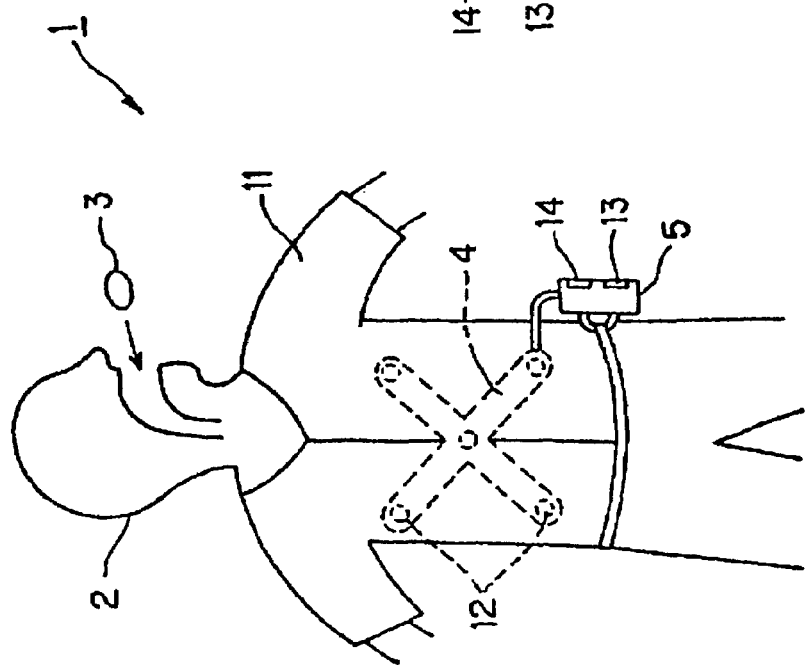
Fig. 1(b)
Fig. 1(a)

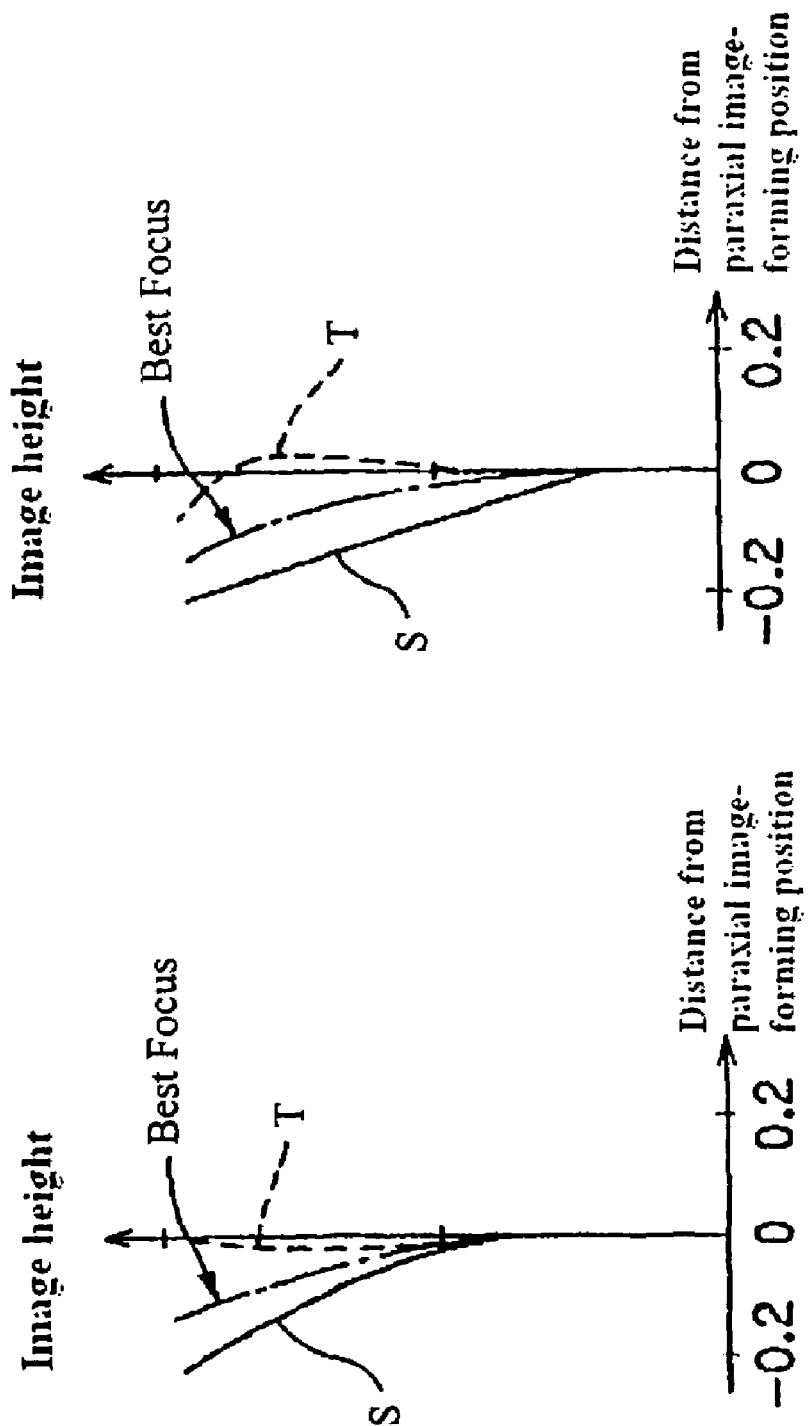

CAPSULE ENDOSCOPE

This application claims the benefit of foreign priority of JP 2003-314707 filed Sep. 5, 2003, the disclosure of which is hereby incorporated by reference.

BACKGROUND OF THE INVENTION

Endoscopes have become widely used in the medical and industrial fields. Also, recently in the medical field, a capsule endoscope that may be swallowed by a patient has been introduced. Such capsule endoscopes are disclosed in Japanese Laid-Open Patent Application 2001-91860 and in International Patent Publication WO 01/65995 A2, and they are advantageous in that they avoid the pain associated with inserting a conventional endoscope's insertion portion.

In Japanese Laid-Open Patent Application 2001-91860, illumination means such as LED's are installed on either side of an objective lens within a transparent cover having a nearly hemispherical shape, and a portion of an object that is illuminated by the light emitting diodes is imaged by the objective lens onto an image sensor. The arrangement of components in the capsule endoscope disclosed in International Patent Publication WO 01/65995 A2 has a similar construction as that discussed above for Japanese Laid-Open Patent Application 2001-91860.

In these prior art examples, an objective lens and an illuminating means are fixed within a transparent cover having a nearly hemispherical shape and, because the radius of curvature of the transparent cover is the same at both the center of the field of view and at the periphery of the field of view, there has been an inconvenience in that the mucosa of lumen organs easily adheres to the central part of the transparent cover. Also, in the case of a transparent cover having a nearly hemispherical shape, because the radius of curvature is determined by the outer diameter of the capsule that connects to the transparent cover, there has been the inconvenience that the overall length of the capsule endoscope becomes large.

Also, no disclosure has been made concerning the performance of an objective optical system as affected by the shape of the observation target or by the focus adjustment condition of the capsule endoscope for providing an optimal observation range.

BRIEF SUMMARY OF THE INVENTION

The present invention relates to a capsule endoscope that may be swallowed by a patient in order to examine internal portions of a living body. More particularly, the present invention enables a capsule endoscope to be miniaturized so as to improve the ease with which it may be swallowed while providing an observation field of view and an observation range that is appropriate for observations using the capsule endoscope.

BRIEF DESCRIPTION OF THE DRAWINGS

The present invention will become more fully understood from the detailed description given below and the accompanying drawings, which are given by way of illustration only and thus are not limitative of the present invention, wherein:

FIGS. 1(a) and 1(b) illustrate various components used to view images of internal portions of a living body using a capsule endoscope;

FIGS. 6(a) and 6(b) show the curvature of field (in mm) for the sagittal image surface S and the tangential image surface T, as well as the surface of 'best focus' of the objective optical systems shown in FIGS. 5(a) and 5(b), respectively;

DETAILED DESCRIPTION

The capsule endoscope of the present invention includes: a light source that illuminates the inside of a living body, an objective optical system that forms an image of a region illuminated by the light source, an image detecting element that captures the image formed by the objective optical system, and a transparent cover that is located in front of the objective optical system. The present invention is characterized by the following Conditions being satisfied:

$$\cos(\theta/2) < a_1/b_1 < 1.0 \quad \text{Condition (1)}$$

$$0.3 \leq \{f^2(1-\cos(\theta/2))/X_B \cdot \cos(\theta/2)\}/|\Delta I| \leq 1.0 \quad \text{Condition (2)}$$

where

θ/2 is the half-field angle, as measured from the optical axis of the objective optical system, that corresponds to the maximum image height of an object;

$a_1$ is the air-equivalent distance along the optical axis of the objective optical system from the front focal point of the objective optical system to the exterior surface of the transparent cover in the on-axis direction;

$b_1$ is the air-equivalent distance from the front focal point of the objective optical system to the exterior surface of the transparent cover in a direction that corresponds to the half-field angle θ/2, as measured from the optical axis;

f is the focal length of the objective optical system;

$X_B$ is the air-equivalent distance from the front focal point of the objective optical system to an object; and ΔI is the average value of the curvature of field of the tangential image surface T and the sagittal image surface S of the objective optical system at the half-field angle θ/2, where θ/2 is measured from the optical axis and the curvature of field is measured from the paraxial image plane.

The present invention enables the size of the capsule endoscope to be reduced while maintaining the same observation field of view and the same object distance that provides the best focus on the optical axis.

Several embodiments of the present invention will now be discussed in detail with reference to the drawings.

Embodiment 1

Figure 2:
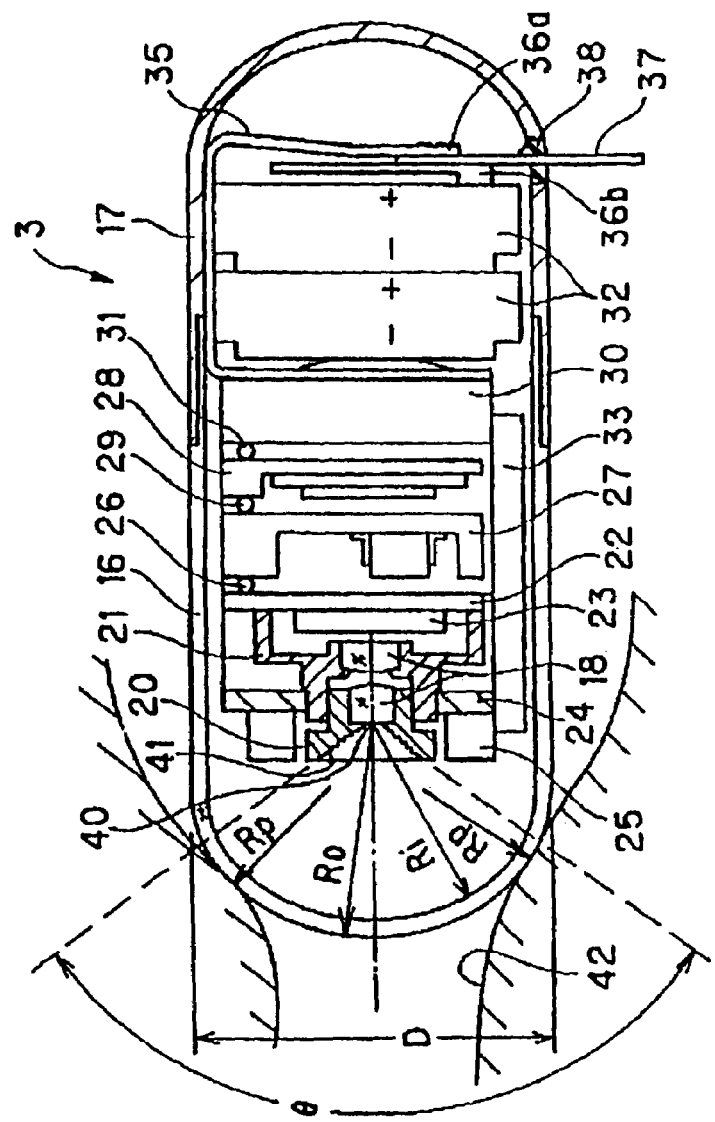
FIG. 2 is a cross-sectional view showing the internal construction of a capsule endoscope according to Embodiment 1.

FIGS. 1(a), 1(b) and 2 relate to Embodiment 1, with FIGS. 1(a) and 1(b) showing various components used to view images of internal portions of a body using a capsule endoscope, and with FIG. 2 showing the construction of a capsule endoscope according to the first embodiment.

As shown in FIG. 1(a), a capsule endoscope apparatus 1 includes a capsule endoscope 3 which transmits by radio signals optical image data of an internal wall of a body cavity passageway as it passes through the body cavity passageway after being swallowed by a patient 2, and an external unit 5 (i.e., that is positioned outside the body of the patient 2) that functions to receive the radio signals transmitted by the capsule endoscope 3. The radio signals are received using an antenna unit 4 that may be, for example, worn by the patient 2. The external unit 5 may contain a memory storage unit such as, for example, a compact flash (R) size memory unit having a 1 GB storage capacity. As shown in FIG. 1(b), image data that is stored in the external unit 5 may be displayed as images by connecting the external unit 5 to a display system 6 either during the transit of the capsule endoscope through the passageway or at a later time.

As shown in FIG. 1(b), the external unit 5 is connected so as to be detachably attachable to a personal computer (PC) 7 that constitutes the display system 6 via a communication cable 8, such as a USB cable. Images stored in the external unit can be received by the PC 7, stored using an internal memory unit such as a hard drive, and the stored images displayed by the display section 9. A keyboard 10 may be connected to the PC 7 for inputting data or commands. As the USB cable 8, any of the communication standards of USB 1.0, USB 1.1, and USB 2 may be used. Alternatively, serial data communication may be used, such as according to the RS-232C, IEEE 1394 communication standard, or other communication standards may be used for parallel or serial communication.

As shown in FIG. 1(a), when performing an endoscopic examination by having the capsule endoscope 3 swallowed by the patient, the antenna unit 4 formed of multiple antennas 12 is fitted inside a shielding shirt 11 that is worn by a patient 2. In this situation, imaging is performed by the capsule endoscope 3, signals sent from the antenna contained within the capsule endoscope are received by the antenna unit 4, and the data is then stored in the external unit 5 which is connected to the antenna unit 4. This external unit 5 may be detachably attached to the belt of the patient 2 by using, for example, a hook. The external unit 5 may have a box-shape, and may include a liquid crystal monitor 13, that serves as a display unit with a control button 14 installed on the front surface of the box for controlling the operation of the external unit and/or the monitor. Inside the external unit 5 may be provided a communication circuit, a control circuit, an image data display circuit, and a power supply.

As shown in FIG. 2, the capsule endoscope 3 forms a sealed water-tight structure by assembling the rear portion of a transparent front cover 16 having a nearly hemispherical shape with a cylindrically-shaped capsule body. The rear cover 17 of the capsule body also has a nearly hemispherical shape. An objective optical system 18 that is formed by attaching a first lens and a second lens to a first lens frame 20 and a second lens frame 21, respectively, is placed so that its image surface is positioned at the image receiving surface of a CMOS image-detecting element 23 that is attached to the front surface of a substrate 22. Also, one or more white LEDs 25 may be attached to a substrate 24 that, in turn, is attached to the second lens frame 21. A substrate 22 which supports the CMOS image detecting element 23 is electrically connected at a connection section 26 to a substrate which supports a driving processing circuit 27.

Also, memory or other electronic components may be formed on the back surface of the substrate which supports the driving processing circuit 27, and a substrate that supports a memory circuit 28 for storing image data is connected by connection section 29. A substrate that supports a wireless communication circuit 30 may be positioned behind the substrate that supports the memory circuit 28, and is positioned to connect with the connection section 31. In addition, two series-connected, button-type batteries 32, 32 may be positioned rearward of the substrate that supports the wireless communication circuit 30. An antenna 33 that is connected to the wireless communication circuit may be placed inside the capsule endoscope adjacent the substrate that supports the driving processing circuit 27. A negative pole of one battery may be connected to a ground of the wireless communication circuit 30, and the positive pole of the other battery may be connected to an end of the lead section of a spring contact element 35.

The spring contact element 35 forms part of a connection section 36a on the rear side of the batteries 32, 32. A connection section 36b that is connected to the positive pole of the series-connected batteries 32, 32 is placed adjacent to the connection section 36a. An insulating string-shaped element 37 may be positioned between the conductive members of the circuit, namely, between the connection sections 36a and 36b, so as to cause the circuit to be set to its OFF state.

A part of the insulating string-shaped element 37 is exposed to the outside through a small cut in a valve section (or a rubber plug) 38 that is installed on the rear cover 17, with the connection sections 36a and 36b making electrical contact with each other when the circuit is turned to its ON state by pulling out the insulating string-shaped element 37. When this occurs, the valve section 38 closes so as to maintain the capsule in a water-tight state.

The inner surface and the outer surface of an axially symmetric, dome-shaped section of the front cover 16 are set so as to have constant radii of curvature, Ri and Ro, respectively, within a central region of the field angle range indicated by θ in FIG. 2. In the present embodiment, Ri equals 6.0 mm and Ro equals 6.5 mm, for example, and the centers of curvature of the radii of curvature Ri and Ro are positioned at the axial position of an entrance pupil 40 of light incident onto the objective optical system 18. Thus, in the present embodiment, the thickness of the front cover 16 is uniform within a central region of the field angle range indicated by θ. Near the periphery of the field of view range θ, the radius of curvature Rp of the outer surface of the transparent cover is set to a smaller value than the radii of curvature Ri and Ro. For example, Rp may be set equal to 4.0 mm, so that the transparent cover smoothly connects to the outer diameter of the cylindrical portion of the capsule endoscope. The outer diameter D of the capsule endoscope 3 is set to 11 mm in the present embodiment.

The front side of the first lens frame 20 has a cone shape and is provided with a rough surface 41 that minimizes specular reflections. Also, in the present embodiment, the field angle range θ is about 90°-110°.

Thus, in the capsule endoscope 3 of the present embodiment, the front surface of the front cover 16 has a nearly hemispherical shape (as shown in FIG. 2), and is characterized by the fact that a peripheral radius of curvature (more specifically, the outer-surface radius of curvature Rp) is made smaller than the radii of curvature in the central region of the field of view range of the objective optical system 18 (more specifically, smaller than the inner-surface radius of curvature Ri and the outer-surface radius of curvature Ro). Such a design is advantageous in that it allows the size of the capsule endoscope 3 to be miniaturized while reducing the tendency of the center portion of the transparent cover to stick to the mucosa of lumen organs.

The operation of the present embodiment will now be discussed. By having the periphery of the transparent surface formed with a radius of curvature that is smaller than would be possible if the capsule endoscope were to have a front surface with a single radius of curvature over its entire forward region enables the radius of curvature in the central region of the field of view to be large and the radius of curvature in the peripheral region to be small. This enables a wide observation range to be secured, from a central region (that typically does not make contact with the mucosa 42) to the peripheral region where contact occurs between the capsule endoscope and the mucosa 42.

Also, if the peripheral region is made to have the same radius of curvature as the central region, a shortcoming arises in that the outer diameter of the capsule endoscope becomes too large, making it difficult to swallow, and poorer in terms of mobility within the body. However, by giving the capsule endoscope the structure as in the present embodiment, the capsule size can be miniaturized. More specifically, with the construction shown in FIG. 2, the outer diameter of the capsule (11 mm) can be made smaller than two times the radius of curvature Ro, which is the radius of curvature of the transparent front surface near the center of the field of view. In contrast, if the transparent cover were to have a constant radius of curvature over its front surface, the outer diameter of the capsule endoscope would be 13 mm, making it thicker than the present embodiment. By making the radius of curvature in the central region larger than that at the periphery (this is especially easy to understand in an extreme case where the radius of curvature is infinite in the central region so that the transparent surface is planar in this region), the amount of forward projection of the transparent cover in the central region is suppressed, reducing the total length and improving the ease of swallowing.

Therefore, the present embodiment has the following efficacies: (1) outer diameter and total length can be made small, thereby making the capsule endoscope easy to swallow; and (2) a wide observation field of view can be provided.

Embodiment 2

Figure 3:
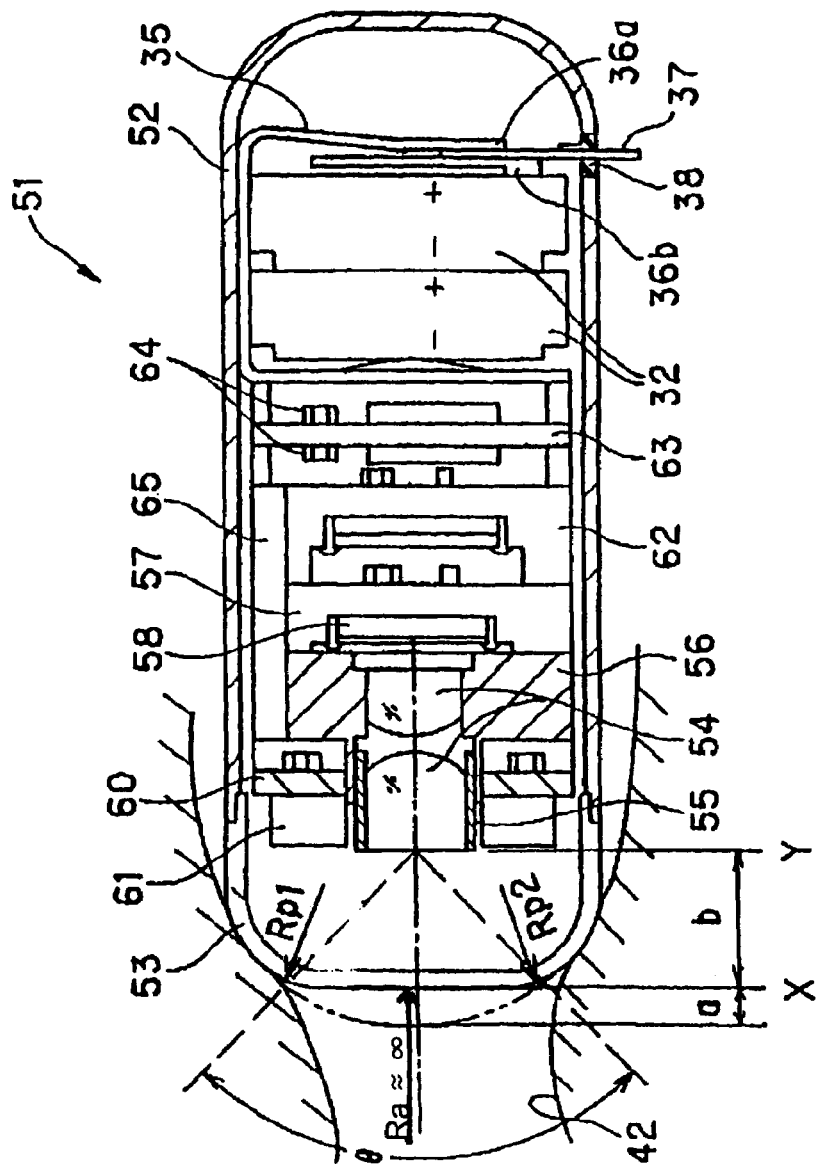
FIG. 3 is a cross-sectional view showing the internal construction of a capsule endoscope according to Embodiment 2.

FIG. 3 shows a capsule endoscope 51 according to Embodiment 2. In the capsule endoscope 51, a rotationally symmetric, transparent cover 53 having a nearly hemispherical shape at its periphery is assembled to a portion of an outer capsule cover 52 which has a cylindrical shape. The rear end portion of the cylinder is occluded, and the front and rear portions of the capsule endoscope body are sealed so as to be water-tight, and enclose an objective optical system 54 as well as other components. The objective optical system 54 is formed by attaching a first lens and a second lens to a first lens frame 55 and a second lens frame 56, respectively. A CMOS image detecting element 58 is mounted within a recess in a substrate 57 at the image forming position of the objective optical system 54. Plural LEDs 61 that emit white light are attached to, and supported by, a substrate 60 that is fixed (by being glued, etc.) onto a cylindrical section of the second lens frame 56. The cylindrical section of the second lens frame 56 surrounds and supports the first lens frame 55.

A substrate that supports a driving, processing, and memory circuit 62 is positioned rearward of the substrate 57 where the CMOS image detecting element is attached. Rearward of the driving, processing, and memory circuit there is a substrate that supports a wireless communication circuit 63. Semiconductor chips 64, 64 are mounted on both sides of the substrate 63.

Two button-type batteries 32, 32 in series arrangement are located rearward of the substrate that supports the wireless communication circuit 63. Also, an antenna 65 that is connected to the wireless communication circuit 63 is positioned within the capsule endoscope adjacent the substrate that supports the driving, processing, and memory circuit 62.

The button-type batteries 32, 32 are connected to a spring-shaped contact element 35 in the same way as explained in FIG. 2, and an insulating string-shaped element 37 is inserted to set it to the OFF state. By pulling out the insulating string-shaped element 37, contact sections 36a and 36b make contact with each other so as to energize the capsule endoscope to the ON state, and a valve section 38 closes so as to maintain the capsule in a water-tight condition.

In the present embodiment, the inner surface and the outer surface of a central region of the transparent cover 53 are provided with a nearly planar surface shape from the center of the field of view to a region near the periphery of the field of view. Thus, the radii of curvature Ra of the inner and outer surfaces are nearly infinity in this region having a field of view θ which spans an angle of about 90° to 110°. As in the previous embodiment, the radii of curvature near the periphery of the field of view θ are smaller than the radius of curvature Ra at the center of the field of view so that the radii of curvature Rp1 and Rp2 connect smoothly with the outer diameter part of the cylindrical portion of the capsule endoscope body. For example, the radii of curvature Rp1, Rp2 in this case are limited to the range of about 1 mm-5 mm. Just as in the previous embodiment, the thickness of the transparent cover 53 is made uniform in the central region of the field of view.

In the present embodiment as shown in FIG. 3, the part to the rear of the two-dot chain line becomes a de-focused region that is out of focus and the part forward of this line becomes a focused region that is in focus in the field of view range θ. In other words, the region within a distance of a+b on the optical axis from the front surface of the first lens of the objective optical system 54 becomes a de-focused region, and objects on-axis that are farther away than the distance a+b on the optical axis from the front surface of the first lens are in focus.

In FIG. 3, the axial position of the front surface of the first lens of the objective optical system 54 on the optical axis is denoted as Y, the axial position of the outer surface of the transparent cover 53 is regarded as X, the distance between X and Y is denoted as 'b', and the distance from the position X to the axial position of the near point of the depth of field is denoted as 'a'. By making the central region of the field of view of the transparent cover 53 a planar shape, the amount of forward projection of the front surface in the central section can be suppressed, and the total length of the capsule endoscope 51 can be reduced. Therefore, ease of swallowing can be improved.

Also, by making the central region of the transparent cover to have a planar shape, it becomes more difficult for the central region of the transparent cover to come in contact with the mucosa 42, thereby ensuring an unobstructed field of view. In this case, although the outer surface position of the transparent cover 53 is not in focus, this presents no practical problem; indeed, it is advantageous in that the overall length of the capsule is reduced by suppressing the amount of forward projection of the transparent cover.

Embodiment 3

Figure 4A:
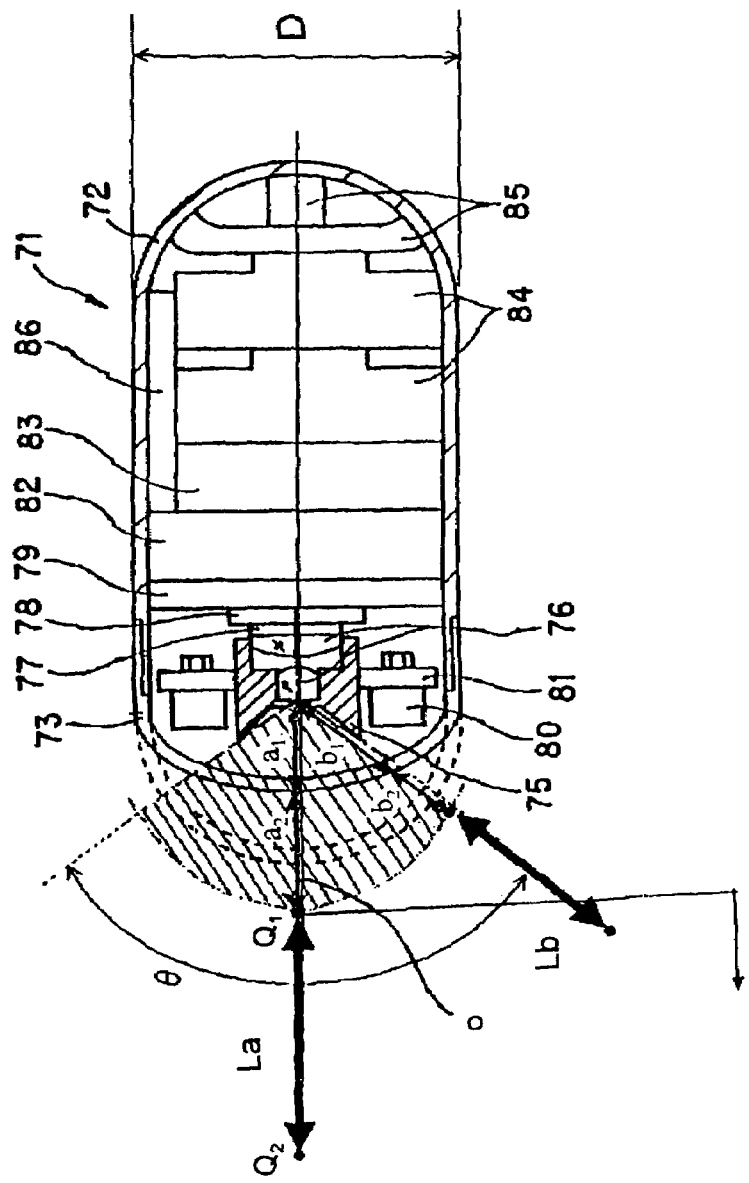
FIGS. 4(a) and 4(b) are cross-sectional views showing the internal construction of a capsule endoscope according to Embodiment 3, with FIG. 4(a) showing the entire capsule endoscope and FIG. 4(b) showing an expanded view of a portion of the capsule endoscope of Embodiment 3 near the transparent cover.

FIGS. 4(a)-6(b) relate to Embodiment 3 of the present invention. FIGS. 4(a) and 4(b) are cross-sectional views showing the internal construction of a capsule endoscope according to Embodiment 3, with FIG. 4(a) showing the entire capsule endoscope and FIG. 4(b) showing an expanded view of a portion of the capsule endoscope of Embodiment 3 near the transparent cover. FIGS. 5(a) and 5(b) are cross-sectional views of different objective optical systems that may be used with the present invention, and FIGS. 6(a) and 6(b) show the curvature of field (in mm) for the sagittal image surface S and the tangential image surface T, as well as the surface of 'best focus' of the objective optical systems shown in FIGS. 5(a) and 5(b), respectively.

In the capsule endoscope 71 shown in FIG. 4(a), a transparent cover 73 has a rotationally symmetric shape about an optical axis such that the radii of curvature (as shown in cross-section) near the periphery of the field of view are small compared to the radius of curvature in the center region of the field of view. The broken lines illustrate a hypothetical transparent front cover having a hemispherical shape.

An objective optical system 76 that is attached to and supported by a lens frame 75 is positioned rearward of the transparent cover 73, and a CMOS image detecting element 78 that is protected by a cover glass 77 is placed at the image surface of the objective optical system 76. The CMOS image detecting element 78 may be mounted on the front surface of a substrate 79, for example. Instead of using the CMOS image detecting element 78, a CCD image detecting element may be used. The objective optical system 76 is formed of two plano-convex lenses, and the planar rear surface of the piano-convex lens that is positioned as the rear lens in the objective optical system with its convex surface on the object side is glued to the cover glass 77. When focusing, the lens frame 75 having an inner diameter which matches with the outer diameter of the rear lens is moved along the optical axis O direction for adjustment, and is then fixed with a glue, etc., after the adjustment.

A substrate 81 having one or more white LEDs 80 attached is fixed by fitting a hole installed at the center of the substrate to a surface (such as the outer circumference) of the lens frame 75 that is matched in size so as to support the substrate 81. The substrate 81 has semiconductor chips mounted thereon that form a driving circuit that drives the one or more white LEDs 80 to flash sequentially. Behind the substrate 79 where the CMOS image detecting element 78 is attached, a substrate is placed that supports a driving and processing circuit 82 which processes the output signals and drives the CMOS image detecting element 78.

On the rear side of the substrate that supports the driving and processing circuit 82 there is a substrate that supports a wireless circuit 83 that wirelessly transmits the image signals. To the rear of the wireless circuit substrate there are provided two button-type batteries 84, 84, that are connected in series. A switch 85 for controlling the ON/OFF state of the capsule endoscope from outside the capsule endoscope body is positioned within the capsule endoscope and to the rear of the batteries 84, 84. Also, an antenna 86 is located within the capsule endoscope body adjacent the wireless circuit 83 and the batteries 84, 84.

Figure 4B:
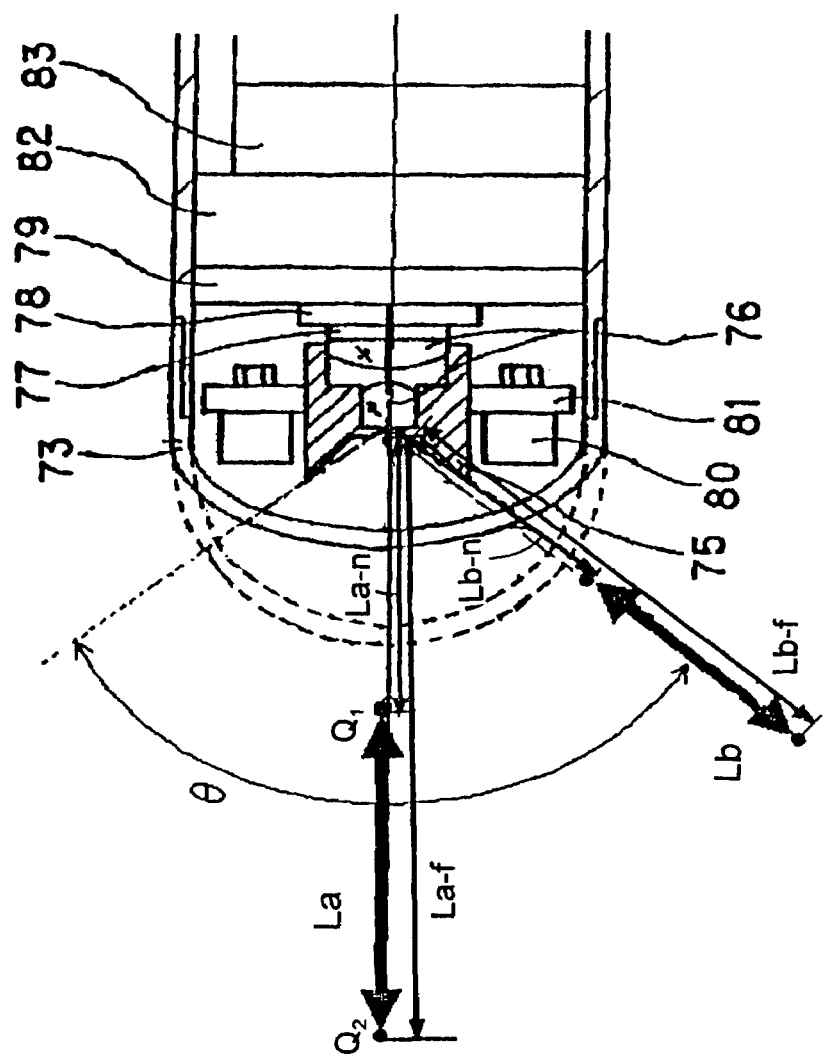
Figure 5A:
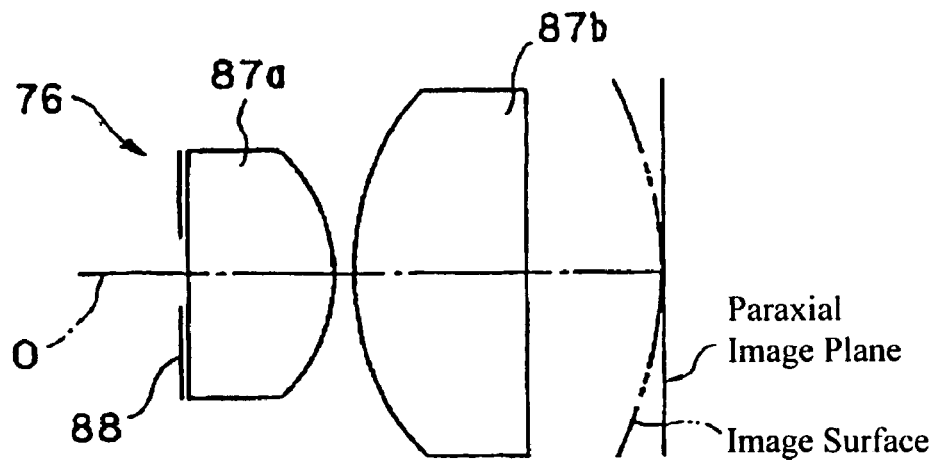
FIGS. 5(a) and 5(b) are cross-sectional views of different objective optical systems that may be used with the present invention.

As shown in FIG. 5(a), a first lens 87a and a second lens 87b of the objective optical system 76 shown in FIGS. 4(a) and 4(b) may be formed of, for example, plano-convex lens elements, with the plano-convex lens element that forms the first lens element 87a having the smaller diameter and being positioned with its planar surface on the object side, and with the plano-convex lens element that forms the second lens element 87b having a relatively larger diameter and being positioned with its planar surface on the image side. An aperture stop 88 is positioned on the object side of the first lens 87a.

Figure 5B:
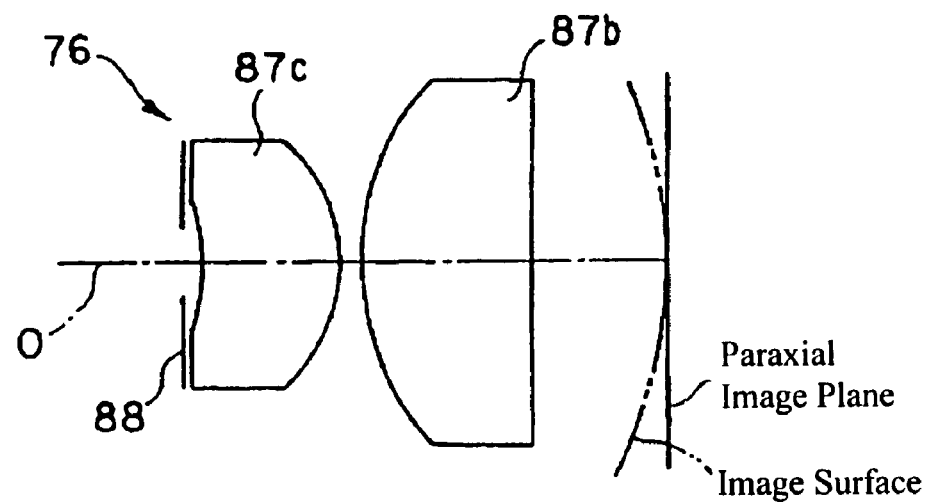

An image is formed by the objective optical system 76 on a planar surface of the CMOS image detecting element 78. FIGS. 5(a) and 5(b) illustrate the image plane at which paraxial rays are imaged, and a representative example of the actual image surface, which typically is concave toward the object side due to the curvature of field of the objective optical system 76.

The spatial relationship between the transparent cover and the depth of field of the objective optical system of Embodiment 3 will now be discussed. FIG. 4(a) is an overall view of a capsule endoscope having an outside diameter D, and FIG. 4(b) is an expanded view of a forward portion of the capsule endoscope shown in FIG. 4(a) near the transparent cover. The labels listed in the figures, and their meanings are as follows:

La is the depth of field along the optical axis;

La-n is the air-equivalent distance along the optical axis from the near point $Q_1$ of the depth of field to the front focal point of the objective optical system 76;

La-f is the air-equivalent distance along the optical axis from the far point $Q_2$ of the depth of field to the front focal point of the objective optical system 76;

$a_1$ is the air-equivalent distance along the optical axis from the front focal point of the objective optical system 76 to the exterior surface of the transparent cover 73;

$a_2$ is the air-equivalent distance along the optical axis from the exterior surface of the transparent cover 73 to the near point $Q_1$ of the depth of field;

$\theta/2$ is the half-field angle (measured from the optical axis) that corresponds to the maximum image height of the objective optical system;

Lb is the depth of field at the half-field angle $\theta/2$;

Lb-n is the air-equivalent distance from the near point of the depth of field to the front focal point of the objective optical system 76 at the half-field angle $\theta/2$;

Lb-f is the air-equivalent distance from the far point of the depth of field to the front focal point of the objective optical system 76 at the half-field angle $\theta/2$;

$b_1$ is the air-equivalent distance from the front focal point of the objective optical system 76 to the surface of the transparent cover 73 at the half-field angle $\theta/2$; and $b_2$ is the air-equivalent distance from the surface of the transparent cover 73 to the near point of the depth of field at the half-field angle $\theta/2$.

Note that the front focal point position of the objective lens 76 in the direction of the field of view center (i.e., along the optical axis) is regarded as the origin point, with the direction toward the object side being positive and the direction toward the image side being negative. In the figure, in the direction along the optical axis O, the region up to the distance $a_1+a_2$ is nearer than the near point of the depth of field and thus is not within the depth of field. Thus, an image of a subject in this range that is captured by the solid-state image-detecting element 78 will not be in focus and will be blurred. In the region La along the optical axis that is within the depth of field, an image of a subject in this range that is captured by the image detecting element 78 will be in focus. Similarly, the region up to the distance $b_1+b_2$ at the half-field angle $\theta/2$ (measured from the optical axis) is nearer than the near point of the depth of field and thus is not within the depth of field. Thus, an image of a subject in this range and viewing angle that is captured by the solid-state image detecting element 78 will be a blurred image that is not in focus. Also, in the region Lb at the half-field angle $\theta/2$ (measured from the optical axis) that is within the depth of field, an image of a subject in this range that is captured by the solid-state image detecting element 78 will be in focus.

In the capsule endoscopes according to the first and second embodiments, the transparent cover is formed with a curvature that varies from the center of the field of view. More specifically, the radius of curvature of the transparent cover surface becomes smaller near the periphery of the field of view as compared to the center of the field of view, such that the following Condition (3) is satisfied:

$$Ro > Rp \quad\quad \text{Condition (3)}$$

where

Ro is the radius of curvature of the object-side surface of the transparent cover on the optical axis of the objective optical system; and Rp is the radius of curvature of the object-side surface of the transparent cover at the periphery of the field of view of the objective optical system.

On the other hand, the shape of the transparent cover of Embodiment 3 is such that the following Condition (4) is satisfied over the range of field angles:

$$Ro = Rp \quad\quad \text{Condition (4).}$$

Thus, Condition (3) is not satisfied by Embodiment 3. However, the following Condition (5) is satisfied by Embodiment (3).

$$\cos(\theta/2) \leq a_1/b_1 < 1.0 \quad\quad \text{Condition (5)}$$

As is apparent from comparing Conditions (1) and (5), Condition (5) differs in its lower limit by allowing the ratio $a_1/b_1$ to equal $\cos(\theta/2)$.

One of the characteristics of the capsule endoscope of the present embodiment is that the transparent cover shape is designed to reduce the overall capsule length. By satisfying the above Condition (1) as in the first and second embodiments, and by satisfying the above Conditions (4) and (5) as in the third embodiment, the transparent cover can be made shorter than, for example, the hemispherical shape that is illustrated in FIGS. 4(a) and 4(b) using dashed-lines.

As mentioned above, the lower limit of Condition (5) is such that $b_1$ equals $a_1$ divided by $\cos(\theta/2)$. Even if the transparent cover is made more flat, the effect on reducing the overall capsule length will not be significant.

Also, if the upper limit of Conditions (1) and (5) is exceeded, the result is that $b_1$ equals $a_1$, in which case the transparent cover becomes hemispherical in shape, and the effect of reducing the overall capsule length can not be obtained.

Unlike conventional endoscopes, capsule endoscopes do not have any mechanism for sending air into organs during a diagnosis. Therefore, there is little chance of observing a flat object by keeping the capsule endoscope at some small distance away from the object of interest, as is possible with conventional endoscopes. Moreover, it is often the case that the inner walls of tube-shaped organs abut the front peripheral surface of the capsule endoscope, as illustrated in FIGS. 2 and 3.

On the other hand, although there are open spaces such as in the stomach where, to some extent a capsule endoscope can be moved both in the forward-backward and right-left directions, even in such a case, observations are often performed in a state where a part of the capsule is in direct contact with an inner wall of an organ. Thus, there is very little probability of being able to observe, for example, the inner wall of the stomach as a nearly planar surface that is positioned ahead of the capsule endoscope by capturing an image of the wall in the direction of the center of the field of view of the objective optical system. Considering this, it is desirable to consider as a typical observation object of interest an object having a spherical shape which abuts the forward peripheral portion of the capsule endoscope.

Figure 9A:
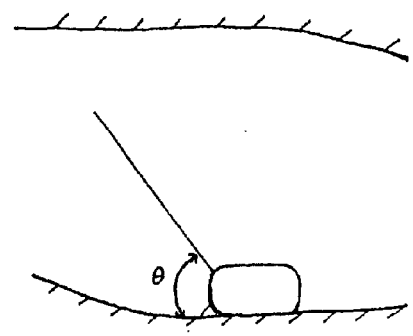
FIGS. 9(a) and 9(b) illustrate the observation range of a capsule endoscope within, for example, the large intestine with the capsule endoscope adjacent one wall thereof, with FIG. 9(b) being an enlarged view and showing greater detail of what is illustrated in FIG. 9(a)
Figure 9B:
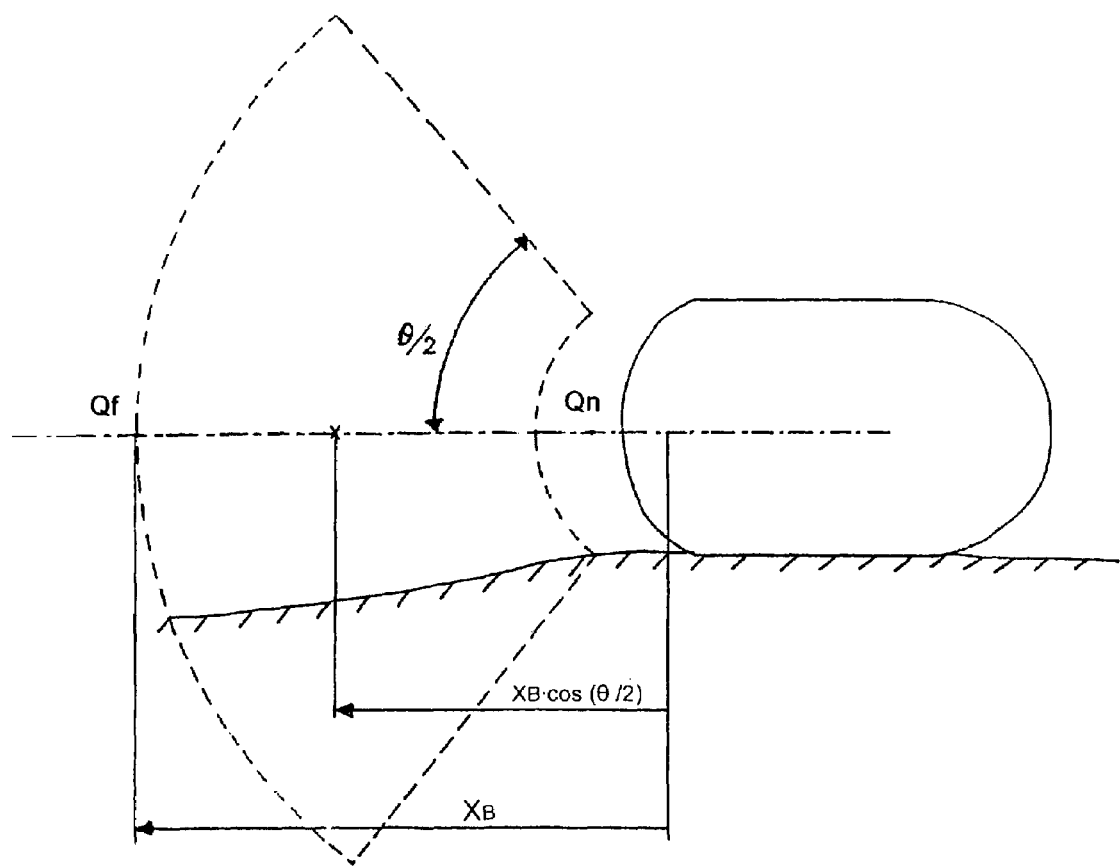

FIG. 9(a) illustrates a capsule endoscope inside a stomach and positioned adjacent a wall of the stomach, and FIG. 9(b) is an expanded view of a portion, near the capsule endoscope, of what is illustrated in FIG. 9(a) but in more detail. More specifically, in FIG. 9(b) the observation range that may be clearly imaged by the capsule endoscope is illustrated. In a capsule endoscope, it is important that, when an object exists between the far point Qf and the near point Qn in the direction of the optical axis of the objective optical system, the object will be clearly observed in that range. Objects that are nearer than the near point of the field of view Qn are not considered to be within the observation range, for reasons that will be discussed later.

Figure 7A:
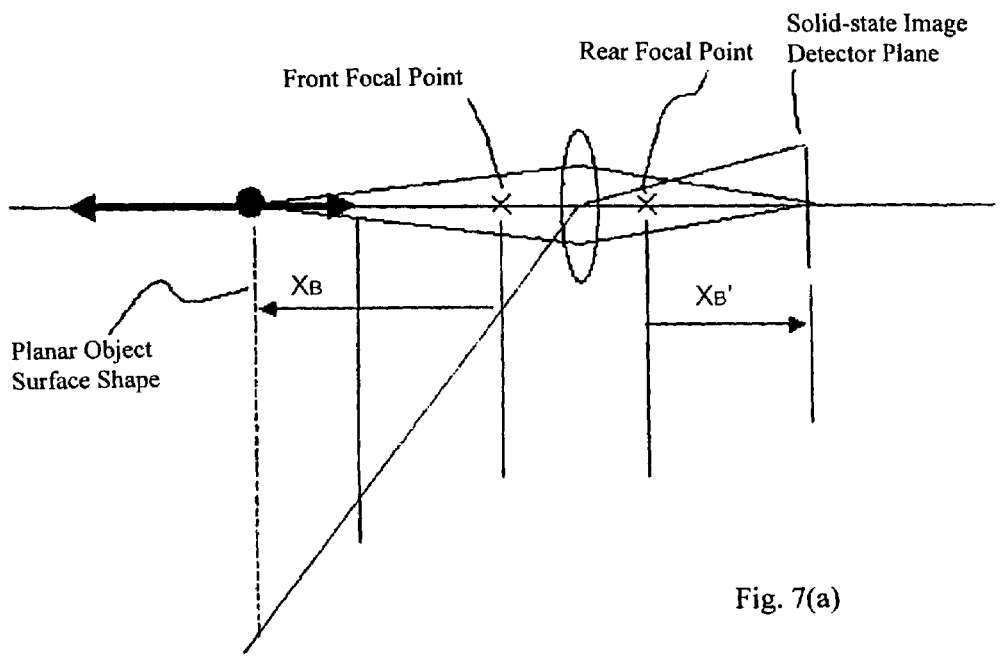
FIGS. 7(a) and 7(b) illustrate imaging by an objective optical system under two different conditions, with FIG. 7(a) illustrating the imaging of a planar object placed in the 'best focus' position on the optical axis when imaged using an objective optical system having its curvature of field well-corrected so as to produce an image surface that is planar, and with FIG. 7(b) illustrating the imaging of a spherical object that is placed in the 'best focus' position on the optical axis of the same objective optical system as used in FIG. 7(a)
Figure 7B:
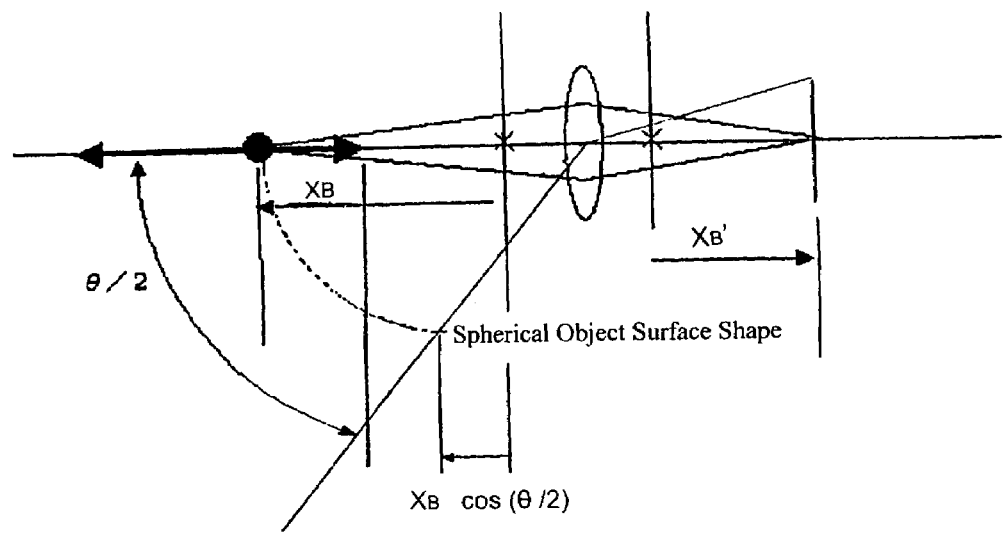

The objective optical system 76 of Embodiment 3 has aberration characteristics that are optimal for viewing an object of a spherical shape. This will now be explained using FIGS. 7(a) and 7(b). FIGS. 7(a) and 7(b) are illustrations that show the relationship between depth of field (in object space) and depth of focus (in image space) of an image detecting unit formed of a typical objective optical system wherein curvature of field is corrected. To the left in the figures is the object side (i.e., object space), and to the right in the figures is the image side (i.e., image space). A solid-state image-detecting element, such as a CCD, is placed at the paraxial image plane of the objective optical system. In FIGS. 7(a) and 7(b) the spatial relationships of all the components except the object surface are the same, and by comparing FIGS. 7(a) and 7(b), the relationship between the depth of field in object space and the depth of focus in image space can be compared.

In an image detecting unit such as in FIGS. 7(a) and 7(b), the depth of field on the object side is determined by the image-forming performance of the objective optical system and the resolution of the solid-state image detecting element. When the depth of field is converted to its conjugate points in image space, what is generally known as the depth of focus, including the central position of the depth of focus and the positions on both ends of the depth of focus can be defined. The central position of the depth of focus is the paraxial image plane position of the objective optical system for the object of interest, and positions exist at both ends of the depth of focus that are equidistant in front of, and to the rear of, the central position of the depth of focus.

The object-side conjugate position of the central position of the depth of focus is called the 'best focus' position, and the object-side conjugate positions of the limits of the depth of focus are called the 'far-point' and the 'near-point' positions of the depth of field. Also, the distance from the front focal point to the 'best focus' position on the optical axis of the objective optical system is called the 'best working distance' (or the 'best distance'). Similarly, the distances to the far-point position or the near-point position of the depth of field as measured from the front focal point are called the far-point distance and the near-point distance, respectively, of the depth of field. Note that when the "best distance at the half-field angle θ/2" or "the object point at the half-field angle θ/2" in the description below is used, these terms indicate air-equivalent distances as measured along the optical axis, with θ/2 being measured from the optical axis.

FIG. 7(a) illustrates the case where imaging is performed by placing a planar object that is at the 'best focus' position ($X_B$, as measured from the front focal point) on the optical axis of an image detecting unit that is equipped with an objective optical system for which the curvature of field has been corrected. Because the object is planar with its surface normal aligned with the optical axis and because the objective optical system has been corrected so that there is zero curvature of field, the 'best focus' position at the half-field angle θ/2 (measured from the optical axis) coincides with the 'best focus' position in the center of the field of view. The dotted-line that is at the distance $X_B$ from the front focal point along the optical axis and that is perpendicular to the optical axis in FIG. 7(a) represents the 'best focus' position over the entire field of view. Thus, a planar object that is positioned with its surface normal aligned with the optical axis can be imaged with a high resolution from the field of view center to the periphery of the field of view. Moreover, even when the planar object is moved from the 'best focus' position, as long as it remains within the range of the depth of field, it will be 'in focus' at the solid-state image detecting element plane, which is at a distance $X_{B'}$ as measured from the rear focal point. Therefore, the image resolution of such an object will not decrease noticeably from the field of view center to the periphery of the field of view.

FIG. 7(b), on the other hand, illustrates the case where a spherical object is placed at the 'best focus' position $X_B$ on the optical axis (as measured from the front focal point of the same optical system as shown in FIG. 7(a)). In this state, resolution at the periphery of the field of view decreases significantly compared with that at the center of the field of view, and no planar image exists in image space that can be acquired as being in focus by the planar image-receiving surface of a solid-state image detecting element. For a spherical object, it is desirable to set the aberration performance of the objective optical system so that the 'best focus' distance at the half-field angle θ/2 (measured from the optical axis) is $X_B \cdot \cos(\theta/2)$.

For example, in FIG. 9(b), when the 'best focus' position in the center of the field of view (i.e., on the optical axis) is set to the point Qf and the distance of this point from the front focal point of the objective optical system is denoted as $X_B$, it is desirable to set the 'best focus' for the half-field angle θ/2 (measured from the optical axis) equal to the distance $X_B \cdot \cos(\theta/2)$ or nearer the image side than such a distance. In this manner, aberration performance of the objective optical system can be optimized for the object shapes most likely to be of interest when using a capsule endoscope. The Newtonian form of the image equation gives the following Equation (A):

$$f/\beta = X_B \qquad \text{Equation (A)}$$

where f is the focal length of the objective optical system;

β is the magnification of the objective optical system for an object on the optical axis at the distance $X_B$ from the front focal point; and $X_B$ is the object point distance on the optical axis as measured from the front focal point when observing a spherical object.

On the other hand, because the object point distance at the half-field angle θ/2 when observing a spherical object is equal to $X_B \cdot \cos(\theta/2)$, the following Equation (B) applies:

$$f/\beta' = X_B \cdot \cos(\theta/2) \qquad \text{Equation (B)}$$

where

β' is the magnification of the objective optical system when observing a spherical object at the half-field angle θ/2 (measured from the optical axis), and $X_{B'}$ is the distance in image space from the rear focal point to the plane of the solid-state image detecting element.

Therefore, the maximum amount of deviation along the optical axis in image space between image points that correspond to two object points when observing a spherical object is given by the following Equation (C):

$$|f_\beta - f_{\beta'}| = f^2(1 - \cos(\theta/2))/X_B \cdot \cos(\theta/2) \qquad \text{Equation (C)}$$

where $f_\beta$ is the image position, as measured from the rear focal point of the objective optical system, that corresponds to the point on the object that is on the optical axis;

$f_{\beta'}$ is the image position, as measured from the rear focal point of the objective optical system, that corresponds to the point on the object that is at the half-field angle θ/2; and f, θ/2, and $X_B$ are as defined previously.

If the curvature of field of the objective optical system is equal in amount and opposite in sign to the maximum deviation of the object surface when imaging a spherical object, the deviation of the image surface when observing such a spherical object can be made to be zero. Thus, if the amount of curvature of field that is generated is given by ΔI as set forth in Equation (D) below, and is opposite in sign to the deviation of the object surface, the deviation of the image surface from the center of the field of view to the maximum image height of the spherical object will be zero:

$$|\Delta l|=|f_\beta-f_\beta'| \quad \text{Equation (D).}$$

If the right side of Equation (D) is substituted into Equation (C), one obtains the following Equation (E):

$$|\Delta l|=f^2(1-\cos(\theta/2))/X_B\cdot\cos(\theta/2) \quad \text{Equation (E).}$$

As a certain amount of deviation of the image surface (an amount determined by the depth of field in object space and the magnification of the objective optical system) will not affect the quality of the detected image, the ratio of the right hand side of Equation (E) divided by the left hand side of Equation (E) may vary from unity, as set forth in Condition (2) above.

If the upper limit of Condition (2) above is not satisfied, the distance between the image surface position relative to the object-point position on the optical axis and the image surface position relative to the object-point position at the half-field angle θ/2 becomes large, and a spherical object observed by the capsule endoscope cannot be adequately focused onto the solid-state image detecting element surface. If the lower limit of Condition (2) is not satisfied, the curvature of field becomes too large to secure a sufficient observation range for the object point position at the half-field angle θ/2.

Referring to FIG. 5(a) in which the imaging optical system corrects the curvature of field in imaging a planar object having a normal that is aligned with the optical axis so that, rather than forming an image surface as shown by the broken line that is concave toward the object side, the image surface instead is planar and corresponds to the paraxial image plane shown by the solid line.

In an actual image detecting unit, because the image receiving surface is a plane that is oriented perpendicular to the optical axis, the image detecting unit can better focus an image surface which is concave toward the image side when its position is moved somewhat relative to the position of the paraxial image plane. Thus, enabling the image surface of the objective optical system to be adjusted along the optical axis so that the image receiving plane of the image detecting unit is moved axially relative to the paraxial image plane enables the image detecting surface to be positioned at the 'best focus' position.

Therefore, the objective optical system of Embodiment 3 requires a focus adjustment which enables the depth of field ranges La and Lb to be adjusted and set. After the common shapes and/or likely distances to (as a function of field angle) objects of interest for a capsule endoscope to observe have been defined, such a focus adjustment needs to be performed so that the observation ranges along the optical axis (i.e, the center direction of the field of view) and at the periphery of the field of view are appropriate. Setting the depth of field of the objective optical system will now be explained.

Referring to FIG. 4(b), in setting the focus adjustment for a capsule endoscope, it is important that near distances La-n and Lb-n for the depths of focus La and Lb are farther from the objective optical system than is the outer surface of the transparent front cover, as otherwise, spots and scratches on the transparent cover will be in focus and thus clearly observable. When such spots and scratches on the transparent cover are clearly observable, they are observed as superimposed images with the object of interest. Thus, the inner walls of alimentary canals, etc., will become superimposed with spots/scratches of the transparent cover and may cause a problem with a diagnosis. The transparent front cover is generally formed of a plastic material and so it tends to develop spots and scratches with assembly and use.

Another reason for setting the near point of the objective optical system so that the ranges of focus La and Lb do not include the transparent cover surface is as follows. When the objective optical system satisfies Condition (2) above, the distance between the front transparent cover and the objective optical system becomes short. Moreover, if the near points La-n and Lb-n are so near that they include the transparent cover, this tends to cause the far points La-f and Lb-f to become insufficiently distant, thereby generating an inconvenience in that the center of the field of view may not be in focus when an object of interest is viewed at a distance, and thus lesions may not be noticed in this region of the field of view. This point is explained in greater detail using FIG. 12.

Figure 12:
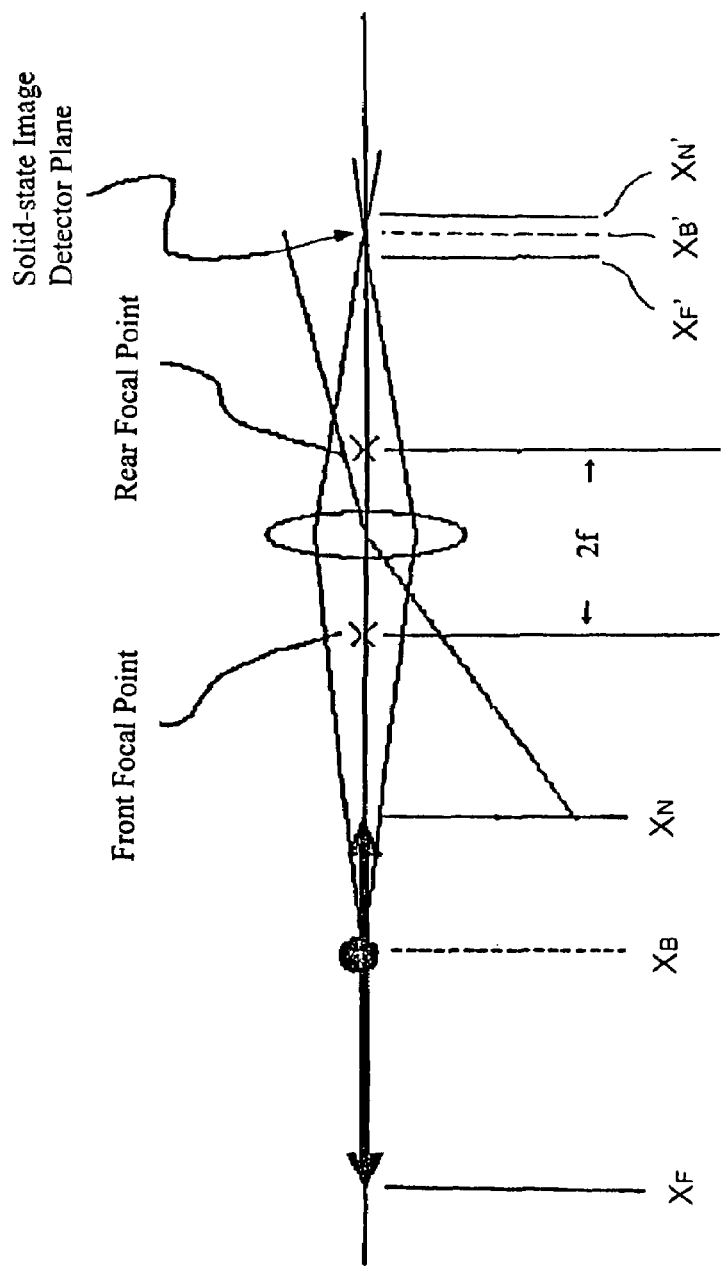
FIG. 12 shows the relationship between depth of field and depth of focus of an objective optical system of an endoscope.

FIG. 12 shows the relationship between depth of field and depth of focus of the objective optical system of a general-use endoscope. In a general-use endoscope, when the 'best focus' position of the depth of field is denoted as $X_B$, the case where a solid-state image detecting element having a pixel pitch p (measured in linear units) is placed at the image plane position $X_{B'}$ will be considered. Considering a state in which the solid-state image detecting element is fixed, the object may be moved inward toward the objective optical system as close to the front focal point position as is the position $X_N$ and still have its image $X_{N'}$ sufficiently in focus so that no deterioration of image quality is observable, since the circle of confusion on the image surface at $X_{N'}$ is no larger than the resolution of the solid-state image detecting element and its associated electronic circuitry. Thus, object positions from the 'best focus' position $X_B$ to the near point position $X_N$ in object space are within the 'depth of field' toward the objective optical system, and the corresponding range of images from $X_{B'}$ to $X_{N'}$ in image space is referred to as the 'depth of focus'. Similarly, the object may be moved away from the front focal point of the objective optical system as far as the position $X_F$ and still have its image $X_{F'}$ sufficiently in focus that no deterioration of image quality is observable, since the circle of confusion on the image surface at $X_{F'}$ is no larger than the resolution of the solid-state image detecting element and its associated electronic circuitry. Thus, object positions from the 'best focus' position $X_B$ to the far point position $X_F$ in object space are within the 'depth of field' away from the objective optical system, and the corresponding points in image space are from $X_{B'}$ to $X_{F'}$. As is well known, the distance from $X_F$ to $X_B$ is larger than the distance from $X_B$ to $X_N$, and the distance from $X_{F'}$ to $X_{B'}$ is larger than the distance from $X_{B'}$ to $X_{N'}$.

From Newton's image equation, the following Equations (F) and (G) hold true for determining the near point $X_N$ of the depth of field and the far point $X_F$ of the depth of field, respectively:

$$1/X_N-1/X_B=K\cdot p\cdot Fno/f^2 \quad \text{Equation (F)}$$

$$1/X_B-1/X_F=K\cdot p\cdot Fno/f^2 \quad \text{Equation (G)}$$

where $X_N$ is the distance from the front focal point to the near point of the depth of field;

$X_B$ is the distance from the front focal point to the 'best focus' position;

$X_F$ is the distance from the front focal point to the far point of the depth of field K is a constant that is determined by the characteristics of the solid-state image detecting element and the associated electronics;

p is the pixel pitch, measured in linear units;

Fno is the f-number of the objective optical system; and f is the focal length of the objective optical system.

The product of K·p gives the resolution, in linear units, of the solid-state image detecting element.

By adding Equations (F) and (G), the following Equation (H) is obtained:

$$1/X_N - 1/X_F = 2 \cdot K \cdot p \cdot Fno/f^2 \quad \text{Equation (H)}.$$

The depth of field as discussed above will now be investigated using actual numerical values for a capsule endoscope. In observing the colon, which among the alimentary-system organs has relatively large void spaces, the far-point distance La-f of the depth of field of the objective optical system on-axis needs to be at least 30 mm. On the other hand, if the near-point distance La-n of the depth of field of the object point that is on the optical axis (i.e., in the center of the field of view) is calculated by tentatively setting the parameters K, p, Fno and f in Equation (H) as K=3, p=5 μm, Fno=5, and f=1, for a capsule endoscope having an outer diameter of 10 mm, the value of La-n, needs to satisfy the following Condition (6):

$$\text{La-n} > 5.45 \text{ mm} \quad \text{Condition (6)}.$$

The manner in which the right hand side of Condition (6) is determined will now be discussed. Because the observation depth range in the periphery of the field of view involves the curvature of field defined by Condition (2) above, the upper limit and lower limit of Condition (2) will be considered:

a) The Upper Limit

Because La-n approximately equals Lb-n where the curvature of field is generated up to about the upper limit of Condition (2) above, when the capsule outer diameter D equals 10 mm, the distance from a hemispherical surface (shown by a broken line in FIG. 10) with its spherical center placed at the first focus point position of the objective optical system to the objective optical system is 5 mm (i.e., D/2).

As shown in FIGS. 4(a) and 4(b), in the capsule endoscope of Embodiment 3, it is required that the relationship shown in the following inequality holds true:

$$Lb\text{-}n > D/2 > b_1.$$

Therefore, since the capsule diameter is 10 mm, $b_2$ (which from FIG. 4(a) equals Lb-n minus $b_1$) must satisfy the following Condition (7):

$$b_2 > 0.45 \quad \text{Condition (7)}.$$

Figure 10:
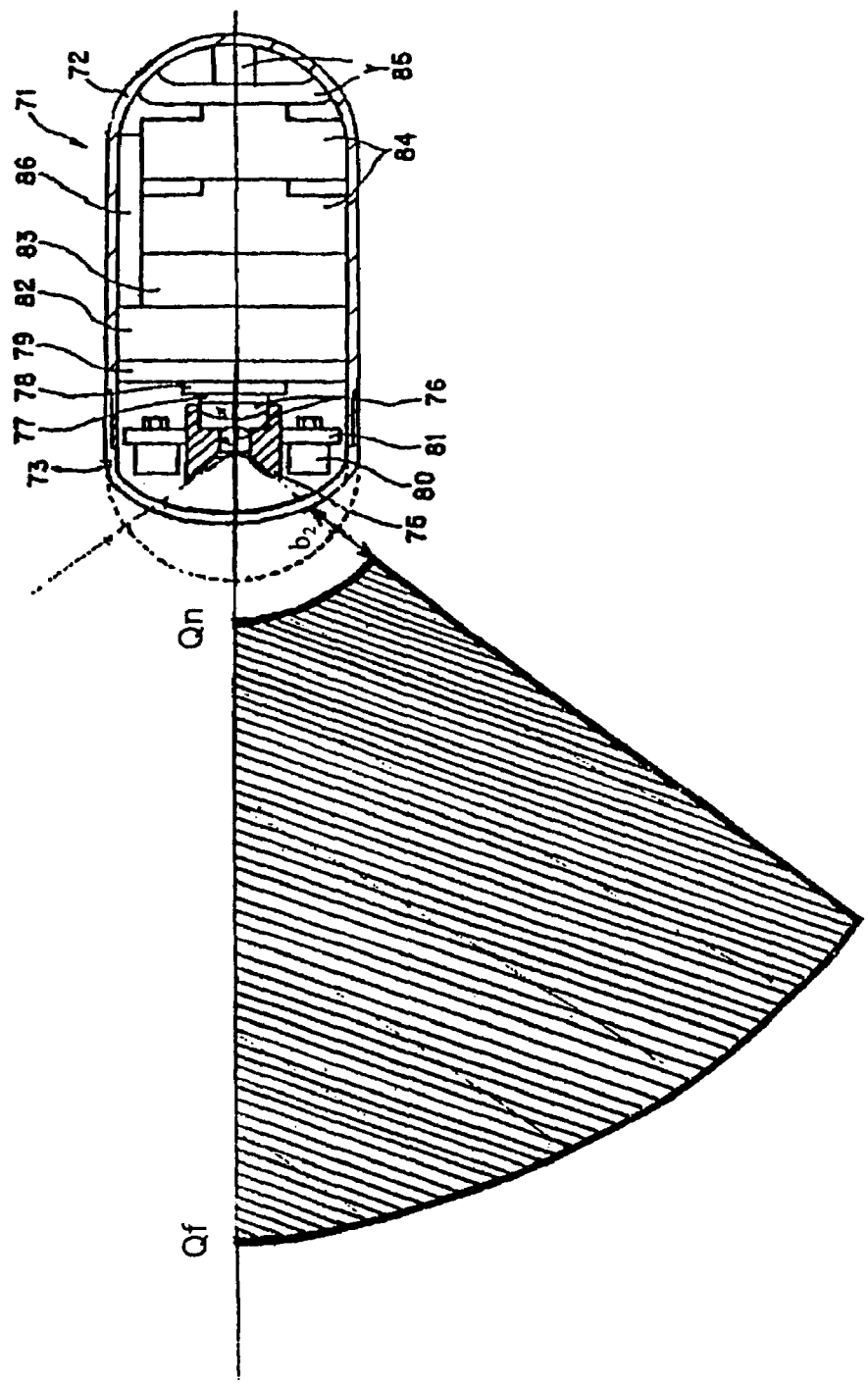
FIG. 10 shows the observation range when focus adjustment of the objective optical system is performed in Embodiment 3 so that the near point of the depth of field at the periphery is an appropriate distance from the transparent cover surface, by setting $b_2$ to an appropriate value, for an optical system where a curvature of field near the upper limit of a specified condition is generated.

By adjusting focus of the image detecting unit so that it satisfies both Condition (6) and Condition (7), the observation range indicated with oblique lines in FIG. 10 can be secured. Namely, if a spherical object of radius of 5 mm is placed on the optical axis with its observation surface within the far-point Qf, (which is at a distance of at least 30 mm from the front focal point) and the near point Qn (which is at a distance of approximately 5.45 mm from the front focal point) it will be observed in focus from its center to its periphery. Also, by placing the near points of the depth of field, over the entire field of view, forward of the transparent cover, spots and scratches on the inside and outside surfaces of the transparent cover will not be in focus in the observation images, and thus will not interfere with a diagnosis.

b) The Lower Limit

Figure 11:
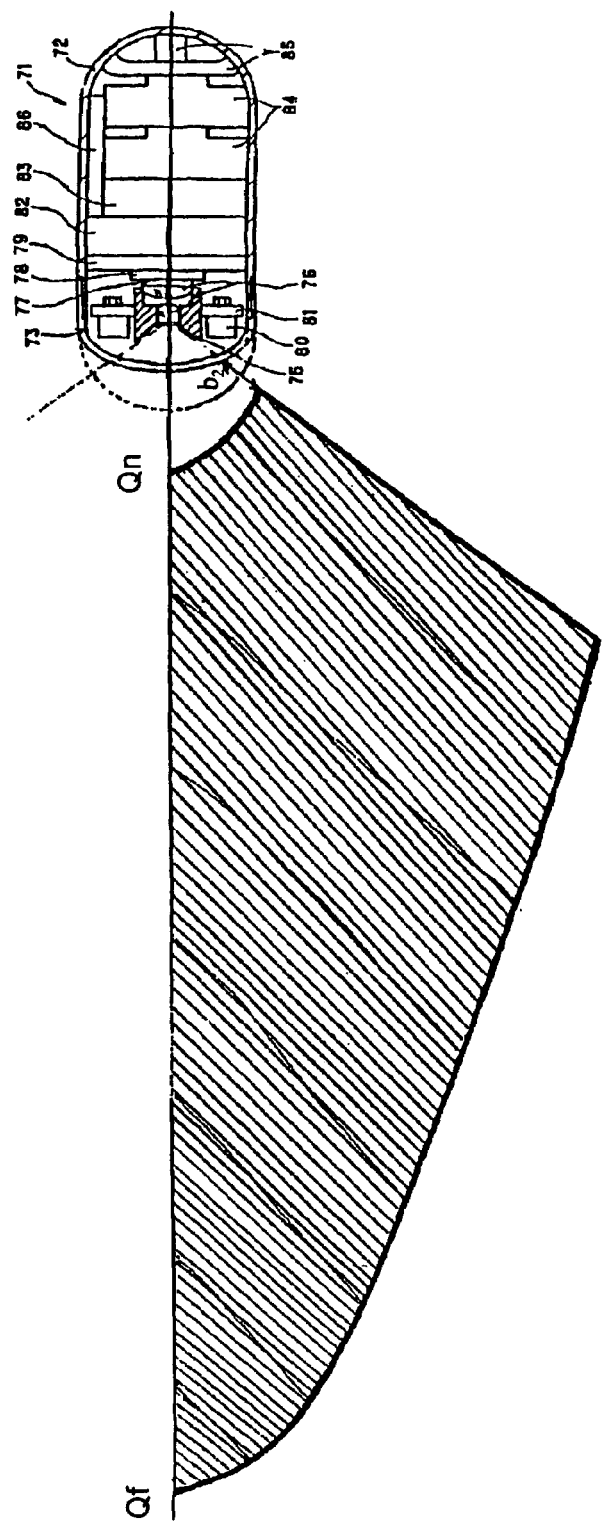
FIG. 11 shows the observation range when focus adjustment of the objective optical system is performed in Embodiment 3 so that the near point of the depth of field at the periphery is an appropriate distance from the transparent cover surface, by setting $b_2$ to an appropriate value, for an optical system where a curvature of field near the lower limit of a specified condition is generated.

In the state in which curvature of field is generated that is about equal to the lower limit of Condition (2) above, because the amount of generated curvature of field increases, if focus adjustment is made so that Condition (7) above is satisfied, then La-n is greater than Lb-n. As noted above, Qf is at a distance of at least 30 mm from the front focal point. Thus La-f is at least 30 mm. In such a case, an observation range indicated by the oblique lines in FIG. 11 is obtained. A capsule endoscope having its observation range set in such a manner is especially effective for observing through voids within tube-shaped organs. Namely, such a capsule endoscope has merit in that it can focus on objects that are quite distant in the direction that the capsule endoscope advances through the tube-shaped organ and can simultaneously focus on the inner walls of the tube-shaped organ at the periphery of the field of view. Thus, there is an opportunity to clearly observe lesions over the entire field of view, and less chance that a lesion that is out of focus near the center of the field of view will be missed.

As per the above discussion, by adopting a transparent cover which satisfies the above Conditions (1) and (2), and by further adopting an objective optical system where the amount of generated curvature of field is equal and opposite to that of the forward surface of the capsule endoscope, and by adjusting the near point of the image detecting unit so that it is forward of the front surface of the transparent cover, with $b_2$ set to zero or greater, a capsule endoscope which is compact and has a good observation performance can be realized.

FIG. 6(a) illustrates the curvature of field for the sagittal image surface S, the tangential image surface T, and for the image surface of 'best focus', which is determined by averaging the curvature of field in the S and T image planes for a given image height for the objective optical system shown in FIG. 5(a). FIG. 6(b) illustrates the curvature of field for the sagittal image surface S, the tangential image surface T, and for the image surface of 'best focus', which is determined by averaging the curvature of field in the S and T image planes for a given image height for the objective optical system shown in FIG. 5(b). In FIG. 5(a), the half-field angle θ/2 of the objective optical system 76 is 45°. In FIGS. 6(a) and 6(b), the horizontal axis indicates the plus or minus distance of the image surface from the paraxial image-forming position, and the vertical axis indicates the image height.

Optical system data of the objective optical system 76 will now be described below. This optical system is formed of two plano-convex lens elements. Because two plano-convex lens elements are easy to manufacture and cost less than, for example, a biconvex lens, such lens elements are attractive for use in an optical system of a capsule endoscope, which is generally disposed of after each use.

Table 1 below lists the construction and performance data of a first example of an objective optical system that may be used in the capsule endoscope according to the present invention. In the top portion of the table are listed, in order from the object side, the surface number #, the radius of curvature R (in mm) of each optical surface, the on-axis spacing D (in mm) between the surfaces, as well as the index of refraction N and the Abbe number υ (both measured relative to the d-line). In the middle portion of the table are listed the focal length f, the front focus distance $f_F$ (the distance from the front focal point to the object side lens surface of the objective optical system), the back focus distance $f_B$ (the distance from the image side lens surface to the rear focal point), the maximum image height IH (in mm), the field angle θ and the value of $X_B$ as defined above. In the bottom portion of the table are listed the values of the change in the sagittal image surface position ΔS and the change in the tangential image surface position ΔT, the absolute value of the average of ΔS and ΔT, as well as the values of the numerator, the denominator, and of the ratio listed in Condition (2) above.

TABLE 1

| # | R | D | N | υ |
|---|---|---|---|---|
| 1 (stop) | ∞ | 0.0 | | |
| 2 | ∞ | 0.845 | 1.51633 | 64.15 |
| 3 | −0.7293 | 0.2391 | | |
| 4 | 1.4689 | 0.9963 | 1.51633 | 64.15 |
| 5 | ∞ | 0.2246 | | |
| 6 (image) | ∞ | 0.0 | | | f = 1.00    $f_F$ = 0.359    $f_B$ = 0.174
IH = 0.727    θ = 88.2°    $X_B$ = 20
ΔS = −0.133    ΔT = 0.013
$f^2 (1 − \cos(θ/2))/X_B \cdot \cos(θ/2)$ = 0.02
|ΔI| = |(ΔS + ΔT)/2| = 0.06
$\{f^2 (1 − \cos(θ/2))/X_B \cdot \cos(θ/2)\}/|ΔI|$ = 0.33

Although other objective optical systems having other properties may be installed in place of the objective optical system 76, such other optical systems should have the same basic properties as those of the objective optical system 76. Futher, specific examples of other such objective optical systems will now be given.

Table 2 below lists the construction and performance data of a second example of an objective optical system that may be used in the capsule endoscope according to the present invention. In the top portion of the table are listed, in order from the object side, the surface number #, the radius of curvature R (in mm) of each optical surface, the on-axis spacing D (in mm) between the surfaces, as well as the index of refraction N and the Abbe number υ (both measured relative to the d-line). In the middle portion of the table are listed the focal length f, the front focus distance $f_F$ (the distance from the front focal point to the object side lens surface of the objective optical system), the back focus distance $f_B$ (the distance from the image side lens surface to the rear focal point), the maximum image height IH (in mm), the field angle θ and the value of $X_B$ as defined above. In the bottom portion of the table are listed the values of the change in the sagittal image surface position ΔS and the change in the tangential image surface position ΔT, the absolute value of the average of ΔS and ΔT, as well as the values of the numerator, the denominator, and of the ratio listed in Condition (2) above.

TABLE 2

| # | R | D | N | υ |
|---|---|---|---|---|
| 1 (stop) | ∞ | 0.0328 | | |
| 2 | ∞ | 0.9849 | 1.79196 | 47.37 |
| 3 | −1.3164 | 0.1094 | | |
| 4 | 1.857 | 0.6018 | 1.79196 | 47.37 |
| 5 | ∞ | 0.6493 | | |
| 6 (image) | ∞ | | | | f = 1.00    $f_F$ = 0.371    $f_B$ = 0.598
IH = 0.72    θ = 90.2    $X_B$ = 20
ΔS = −0.11    ΔT = 0.0
$f^2 (1 − \cos(θ/2))/X_B \cdot \cos(θ/2)$ = 0.02
|ΔI| = |(ΔS + ΔT)/2| = 0.06
$\{f^2 (1 − \cos(θ/2))/X_B \cdot \cos(θ/2)\}/|ΔI|$ = 0.33

Table 3 below lists the construction and performance data of a third example of an objective optical system that may be used in the capsule endoscope according to the present invention. In the top portion of the table are listed, in order from the object side, the surface number #, the radius of curvature R (in mm) of each optical surface, the on-axis spacing D (in mm) between the surfaces, as well as the index of refraction N and the Abbe number υ (both measured relative to the d-line). In the middle portion of the table are listed the focal length f, the front focus distance $f_F$ (the distance from the front focal point to the object side lens surface of the objective optical system), the back focus distance $f_B$ (the distance from the image side lens surface to the rear focal point), the maximum image height IH (in mm), the field angle θ and the value of $X_B$ as defined above. In the bottom portion of the table are listed the values of the change in the sagittal image surface position ΔS and the change in the tangential image surface position ΔT, the absolute value of the average of ΔS and ΔT, as well as the values of the numerator, the denominator, and of the ratio listed in Condition (2) above.

TABLE 3

| # | R | D | N | υ |
|---|---|---|---|---|
| 1 (stop) | ∞ | 0.0 | | |
| 2 | 1.3696 | 0.7689 | 1.49214 | 57.6 |
| 3* | −0.6259 | 0.8663 | | |
| 4 | ∞ (image surface) | | | | f = 1.00    $f_F$ = 0.595    $f_B$ = 0.507
IH = 0.769    θ = 83.8    $X_B$ = 20
ΔS = −0.238    ΔT = −0.337
$f^2 (1 − \cos(θ/2))/X_B \cdot \cos(θ/2)$ = 0.017
|ΔI| = |(ΔS + ΔT)/2| = 0.288
$\{f^2 (1 − \cos(θ/2))/X_B \cdot \cos(θ/2)\}/|ΔI|$ = 0.59

Whereas previous examples used two plano-convex lenses made of glass, this optical system uses a single lens element that is made of plastic. The plastic lens element is designed so that the manufacturing and assembly costs are reduced as compared to using two plano-convex, glass lenses. In this optical system, an aspherical surface is introduced, which enables a single lens element to provide the necessary optical performance needed of the objective optical system.

The asterisk to the right of surface #3 denotes that surface #3 is aspheric. The shape of the aspheric surface is given by Equation (I) below:

$$Z = (y^2/r)/[1 + \{1 − (K+1)(y/r)^2\}^{1/2}] + A_4 y^4 + A_6 y^6 + A_8 y^8 + A_{10} y^{10}$$ Equation (I)

where
Z is the length (in mm) of a line drawn from a point on the aspherical surface at distance y from the optical axis to the tangential plane of the aspherical surface vertex,
r is the radius of curvature of the aspherical surface near the optical axis,
y is the distance (in mm) from the optical axis,
K is the eccentricity, and
$A_4$, $A_6$, $A_8$, and $A_{10}$ are the 4th, 6th, 8th, and 10th aspherical coefficients.

In forming surface #3, the values of the constants K, $A_6$, $A_8$, and $A_{10}$ are zero and the value of $A_4$ is $1.6880 \times 10^{-01}$.

Figure 8A:
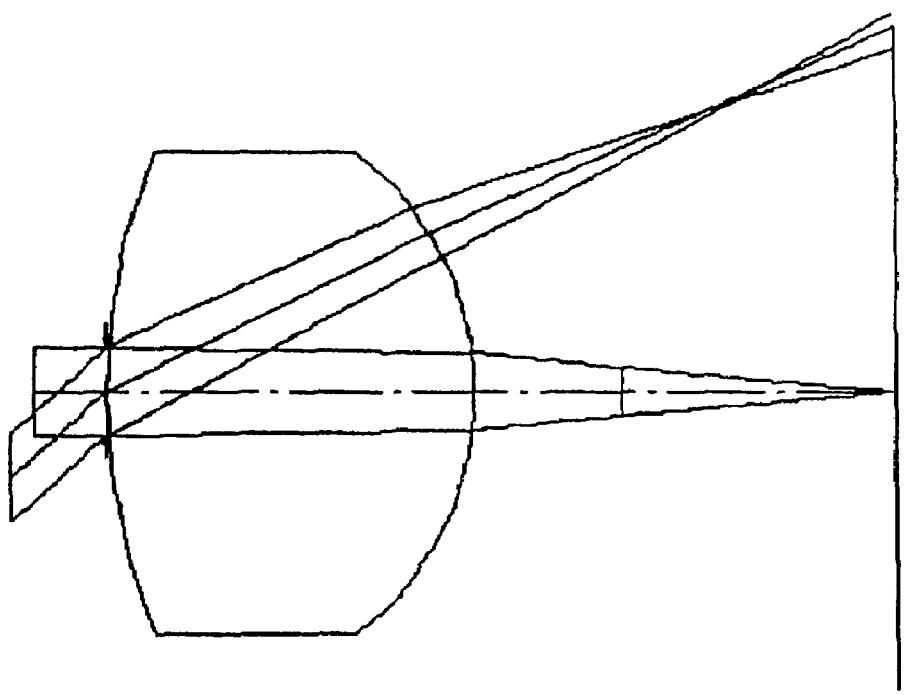
FIG. 8(a) illustrates a possible modification that may be made to the objective optical system of Embodiment 3.
Figure 8B:
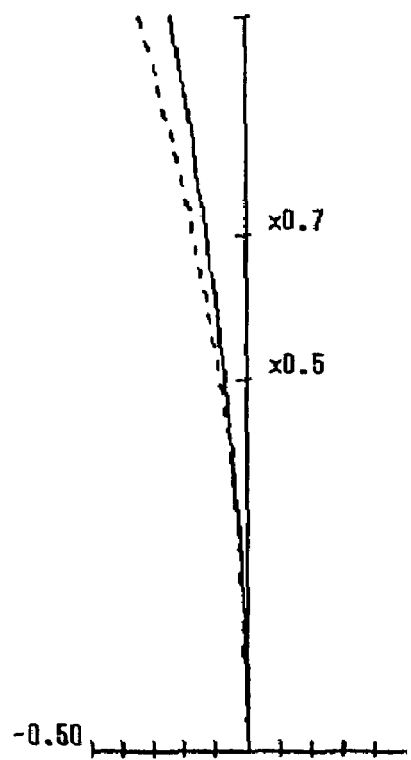
FIG. 8(b) shows the curvature of field of the objective optical system shown in FIG. 8(a)

FIG. 8(*a*) illustrates the form of the objective optical system of this specific example, and FIG. 8(*b*) shows the curvature of field for the sagittal image surface S and the tangential image surface T of this specific example.

In the case of the objective optical system shown in FIG. 5(a), because the aberrations abruptly increase if the half-field angle θ/2 exceeds 45°, when a larger angle of view is desired, it is desirable to use the objective optical system shown in FIG. 5(b).

In FIG. 5(b), a meniscus lens 87c having a rather small outer circumference is adopted as the first lens element in lieu of using the plano-convex lens 87a as used in the objective optical system shown in FIG. 5(a). The meniscus lens 87c has a concave surface on the object side of relatively large radius of curvature, and the meniscus lens 87c has positive overall refractive power.

FIG. 6(b) shows the curvature of field (in mm) for the sagittal image surface S and the tangential image surface T, as well as the surface of 'best focus' of the objective optical system shown in 5(b), which has a half-field angle θ/2 of 60°. In this case, even though the half-field angle θ/2 is larger than in the case of FIGS. 5(a) and 6(a), the curvature of field aberrations are favorably corrected, especially the curvature of field of the 'best focus' image surface.

Next, another specific example of an objective optical system having a half-field angle θ/2 that equals 56°, and with similar properties as the optical systems described above, will be set forth.

Table 4 below lists the construction and performance data of a fourth example of an objective optical system that may be used in the capsule endoscope according to the present invention. In the top portion of the table are listed, in order from the object side, the surface number #, the radius of curvature R (in mm) of each optical surface, the on-axis spacing D (in mm) between the surfaces, as well as the index of refraction N and the Abbe number υ (both measured relative to the d-line). In the middle portion of the table are listed the focal length f, the front focus distance $f_F$ (the distance from the front focal point to the object side lens surface of the objective optical system), the back focus distance $f_B$ (the distance from the image side lens surface to the rear focal point), the maximum image height IH (in mm), the field angle θ and the value of $X_B$ as defined above. In the bottom portion of the table are listed the values of the change in the sagittal image surface position ΔS and the change in the tangential image surface position ΔT, the absolute value of the average of ΔS and ΔT, as well as the values of the numerator, the denominator, and of the ratio listed in Condition (2) above.

TABLE 4

| # | R | D | N | υ |
|---|---|---|---|---|
| 1 (stop) | ∞ | 0.0664 | | |
| 2 | −1.5971 | 1.0304 | 1.883 | 40.76 |
| 3 | −1.062 | 0.0499 | | |
| 4 | 1.396 | 0.8143 | 1.514 | 75 |
| 5 | ∞ | 0.7889 | | |
| 6 (image) | ∞ | | | | f = 1.00    $f_F$ = 0.267    $f_B$ = 0.738
IH = 0.8    θ = 113.6    $X_B$ = 20
ΔS = −0.056    ΔT = −0.045
$f^2 (1 − \cos(θ/2))/X_B \cdot \cos(θ/2) = 0.041$
|ΔI| = |(ΔS + ΔT)/2| = 0.051
$\{f^2 (1 − \cos(θ/2))/X_B \cdot \cos(θ/2)\}/|ΔI| = 0.8$ Although the meniscus lens 87c would ordinarily be more difficult to process than the plano-convex lens 87a, by injection molding a plastic, optical-grade material into the desired shape, the manufacturing cost per unit, at least for large quantity orders, can be significantly decreased. If the plano-convex lens 87b is also injection molded using optical-grade, plastic material, an objective optical system 76 having a low processing cost can be realized.

Thus, this embodiment also provides good image quality while suppressing the amount of forward projection of the transparent cover and reducing the overall capsule endoscope length, while at the same time, the design enables easy swallowing of the capsule endoscope. Furthermore, a processing circuit that processes image signals acquired by the image detecting unit installed within the capsule endoscope may be provided outside the capsule endoscope. Such a processing circuit can, for example, perform distortion correction of images and/or partial expansion of images so as to further improve the image quality.

The invention being thus described, it will be obvious that the same may be varied in many ways. Such variations are not to be regarded as a departure from the spirit and scope of the invention. Rather, the scope of the invention shall be defined as set forth in the following claims and their legal equivalents. All such modifications as would be obvious to one skilled in the art are intended to be included within the scope of the following claims.

What is claimed is:

1. A capsule endoscope comprising:
   a light source;
   an objective optical system that forms an image of an object that is illuminated by the light source;
   an image pickup device that receives the image formed by the objective optical system; and
   a transparent cover that is positioned in front of the objective optical system;
   wherein the following conditions are satisfied:

$\cos(θ/2) < a_1/b_1 < 1.0$ $0.3 \leq \{f^2(1−\cos(θ/2))/X_B \cdot \cos(θ/2)\}/|ΔI| \leq 1.0$ where
   θ/2 is the half-field angle, as measured from the optical axis of the objective optical system, that corresponds to the maximum image height of an object;
   $a_1$ is the air-equivalent distance along the optical axis of the objective optical system from the front focal point of the objective optical system to the exterior surface of the transparent cover in the on-axis direction;
   $b_1$ is the air-equivalent distance from the front focal point of the objective optical system to the exterior surface of the transparent cover in a direction that corresponds to the half-field angle θ/2, as measured from the optical axis;
   f is the focal length of the objective optical system;
   $X_B$ is the air-equivalent distance from the front focal point of the objective optical system to an object; and
   ΔI is the average value of the curvature of field of the tangential image surface T and the sagittal image surface S of the objective optical system at the half-field angle θ/2, where θ/2 is measured from the optical axis and the curvature of field is measured from the paraxial image plane.

2. The capsule endoscope according to claim 1, wherein the following condition is also satisfied:

$b_2 > 0.4$ where
   $b_2$ is the air-equivalent distance from the transparent cover surface to the near point position of the depth of field in a direction corresponding to the angle θ/2, as measured from the optical axis.

3. A capsule endoscope comprising:
- an illumination source;
- an objective optical system that forms an image of an object;
- an image pickup device that receives the image formed by the objective optical system;
- an adjustment device that enables the distance between the objective optical system and the image pickup device to be varied; and
- a transparent cover in front of the objective optical system;

wherein the capsule endoscope satisfies the following conditions:

$$\cos(\theta/2) \leq a_1/b_1 < 1$$

$$b_2 > 0$$

$$0.3 \leq \{f^2(1-\cos(\theta/2))/X_B \cdot \cos(\theta/2)\}/|\Delta I| \leq 1.0$$

where
- $\theta/2$ is the half-field angle, as measured from the optical axis of the objective optical system, that corresponds to the maximum image height of an object;
- $a_1$ is the air-equivalent distance along the optical axis of the objective optical system from the front focal point of the objective optical system to the exterior surface of the transparent cover in the on-axis direction;
- $b_1$ is the air-equivalent distance from the front focal point of the objective optical system to the exterior surface of the transparent cover in a direction that corresponds to the half-field angle $\theta/2$, as measured from the optical axis;
- $b_2$ is the air-equivalent distance from the transparent cover surface to the near point of the depth of field at the half-field angle $\theta/2$, where $\theta/2$ is measured from the optical axis;
- f is the focal length of the objective optical system;
- $X_B$ is the air-equivalent distance from the front focal point of the objective optical system to an object; and
- $\Delta I$ is the average value of the curvature of field of the tangential image surface T and the sagittal image surface S of the objective optical system at the half-field angle $\theta/2$, where $\theta/2$ is measured from the optical axis and the curvature of field is measured from the paraxial image plane.

4. The capsule endoscope according to claim 3, wherein the following condition is also satisfied:

$$b_2 > 0.4$$

5. The capsule endoscope according to claim 3, wherein La-f, which is the air-equivalent distance from the far point of the depth of field along the optical axis to the front focal point of the objective optical system, is at least 30 mm.

6. The capsule endoscope according to claim 4, wherein La-f, which is the air-equivalent distance from the fur point of the depth of field along the optical axis to the front focal point of the objective optical system, is at least 30 mm.

7. The capsule endoscope according to claim 3, wherein the objective optical system includes a piano-convex lens.

8. The capsule endoscope according to claim 4, wherein the objective optical system includes a piano-convex lens.

9. The capsule endoscope according to claim 5, wherein the objective optical system includes a piano-convex lens.

10. The capsule endoscope according to claim 6, wherein the objective optical system includes a plano-convex lens.

11. The capsule endoscope according to claim 3, wherein the objective optical system includes at least one lens element that is made of optical-grade plastic and has at least one aspherical surface.

12. The capsule endoscope according to claim 4, wherein the objective optical system includes at least one lens element that is made of optical-grade plastic and has at least one aspherical surface.

13. The capsule endoscope according to claim 5, wherein the objective optical system includes at least one lens element that is made of optical-grade plastic and has at least one aspherical surface.

14. The capsule endoscope according to claim 6, wherein the objective optical system includes at least one lens element that is made of optical-grade plastic and has at least one aspherical surface.

15. The capsule endoscope according to claim 3, wherein the objective optical system includes a positive meniscus lens.

16. The capsule endoscope according to claim 4, wherein the objective optical system includes a positive menisscus lens.

17. The capsule endoscope according to claim 5, wherein the objective optical system includes a positive meniscus lens.

18. The capsule endoscope according to claim 6, wherein the objective optical system includes a positive meniscus lens.

19. The capsule endoscope according to claim 3, and further comprising a wireless transmission circuitry for transmitting an image signal being output from the image pickup device.

20. The capsule endoscope according to claim 4, and further comprising a wireless transmission circuitry for transmitting an image signal being output from the image pickup device.

* * * * *